(12) United States Patent
Andrali et al.

(10) Patent No.: US 9,737,551 B2
(45) Date of Patent: Aug. 22, 2017

(54) BERBERINE-URSODEOXYCHOLIC ACID CONJUGATE FOR TREATING THE LIVER

(71) Applicant: NORTH AMERICAN BIOMEDICAL RESEARCH CENTER USA, INC., Los Angeles, CA (US)

(72) Inventors: Shiva Sreenath Andrali, Los Angeles, CA (US); Venkatesh Tekumalla, Hyderabad (IN)

(73) Assignee: North American Biomedical Research Center USA, Inc., Los Angeles, CA (US)

( * ) Notice: Subject to any disclaimer, the term of this patent is extended or adjusted under 35 U.S.C. 154(b) by 0 days.

(21) Appl. No.: 15/426,793

(22) Filed: Feb. 7, 2017

(65) Prior Publication Data
US 2017/0143742 A1    May 25, 2017

Related U.S. Application Data

(63) Continuation-in-part of application No. 15/077,661, filed on Mar. 22, 2016, now Pat. No. 9,597,337, which is a continuation-in-part of application No. 14/864,226, filed on Sep. 24, 2015, now abandoned, which is a continuation of application No. 14/245,722, filed on Apr. 4, 2014, now abandoned.

(51) Int. Cl.
*A61K 31/4745* (2006.01)
*A61K 31/58* (2006.01)
*A61K 9/00* (2006.01)

(52) U.S. Cl.
CPC ............ *A61K 31/58* (2013.01); *A61K 9/0019* (2013.01); *A61K 9/0053* (2013.01)

(58) Field of Classification Search
CPC ........................... A61K 31/4745; A61K 31/58
USPC ........................................................ 514/280
See application file for complete search history.

(56) References Cited

U.S. PATENT DOCUMENTS 9,597,337 B2 *  3/2017  Andrali ................. C07J 43/003

FOREIGN PATENT DOCUMENTS

CN           102225961 A      10/2011

* cited by examiner

*Primary Examiner* — Charanjit Aulakh
(74) *Attorney, Agent, or Firm* — Hankin Patent Law, APC; Kevin Schraven; Anooj Patel

(57) ABSTRACT

The present invention is a method and compound for treating specific cancerous cell lines. The invention treats liver cancer by directing a cancer-fighting drug into the liver hepatoportal circuit. The cancer-fighting drug is attached to a naturally produced molecule which functions primarily in the hepatoportal circuit and has organotropism for the hepatoportal circuit.

10 Claims, 9 Drawing Sheets

BERBERINE-URSODEOXYCHOLIC ACID CONJUGATE FOR TREATING THE LIVER

CROSS-REFERENCE TO RELATED APPLICATIONS

This Continuation-In-Part Patent Application claims the benefit of U.S. Non-Provisional patent application Ser. No. 15/077,661, filed on Mar. 22, 2016, titled "BERBERINE-URSODEOXYCHOLIC ACID CONJUGATE FOR TREATING THE LIVER," by inventors Shiva Sreenath Andrali and Venkatesh Tekumalla, which claims the benefit of U.S. Non-Provisional patent application Ser. No. 14/864,226, filed on Sep. 24, 2015, titled "BERBERINE-URSODEOXYCHOLIC ACID CONJUGATE FOR TREATING THE LIVER," by inventors Shiva Sreenath Andrali and Venkatesh Tekumalla, which claims the benefit of U.S. Non-Provisional patent application Ser. No. 14/245,722, filed on Mar. 4, 2014, titled "BERBERINE-URSODEOXYCHOLIC ACID CONJUGATE FOR TREATING THE LIVER," by inventors Shiva Sreenath Andrali and Venkatesh Tekumalla, the contents of which are expressly incorporated herein by this reference as though set forth in their entirety.

FIELD OF INVENTION

This invention relates to a method and molecule for treating solid tumors. More particularly, the invention relates to the synthesis of and molecule, berberine-ursodeoxycholic acid conjugate, herein referred to as NAB03, for specifically targeting and treating cancerous liver cells. NAB03 is easily administered, increases effectiveness, and may lower negative side-effects relative to other available liver ailment and cancer fighting techniques.

BACKGROUND

For centuries, people have attempted to cure ailments and diseases with whatever means they had available at the time. Initially, this could include rituals or sacred procedures. As time progressed, people started to discover the efficacy of certain herbs, roots, and other naturally occurring substances in the treatment of ailments. As civilization progressed even further, science allowed for humans to discover what made the herbs and roots so effective. Useful and effective compounds were identified, isolated, purified, and administered with great efficacy in the treatment of diseases.

People then discovered they could actually create compounds, based both on knowledge gleaned from their past in combination with knowledge gained from scientific experimentation. With this new creative ability, diseases were fought on massive scales, and deaths as a result dropped drastically. As of now, two diseases were even fought to eradication, smallpox and rinderpest, and numerous other diseases are believed to be just a few years away from eradication. Yet, certain diseases are more difficult to treat, and some are even the result of an individual's behavior, so they cannot be eradicated purely through the use of treatment. In many cases, they must be fought as they appear in the individual.

Of particular importance is the human liver. The liver is has a myriad of functions in the body which comprises cleaning toxins from blood, regulating bodily functions, producing substances for proper digestion, producing regulatory signal molecules, and even facilitating blood clotting. The liver also has the unique ability to function even if a significant portion has been removed. However, with the myriad of functions performed by the liver, there are also a myriad of ailments which may affect the liver and its ability to function.

There are a myriad of ailments that may be experienced due problems in the liver which comprises cancer, cirrhosis, primary sclerosing, cholangitis, cholelithiasis, non-alcoholic fatty liver disease, non-alcoholic steatohepatitis, high cholesterol, cardiovascular conditions and diabetes. Various medicines and treatments have been created in order to combat these conditions, but they experience similar issues as other medicines and treatments. Through diligent research and enormous efforts, many useful molecules have been and are being discovered. This may have resulted in a double edged sword, as now there are a voluminous amount of useful molecules or suspected useful molecules, but as a consequence, there are virtually an infinite number of combinations using these molecules. Certain molecules or drugs have beneficial effects when combined with other molecules, but without going through rigorous experimentation, often including costly and expensive human trials, many of these combinations are, and will remain, undiscovered. The problem with combining molecules, however, is that the results can be hard to predict, and in many cases can cause more harm than good. Many drugs may be used subsequently without disastrous side-effects, but concurrently taking an effective dose of that same drug can result in serious side-effects, including death. As a result, experimentation must be done slowly and deliberately which may result in discovering non-useful formulations. The cost and danger associated with experimentally combining different drugs in a patient can be both extremely costly, and more importantly, extremely dangerous.

Further, although it is known that combining different molecules in a single drug treatment compound is theoretically possible, it is not possible to predict with certainty what the combination may do. Because there are a multitude of biochemical pathways in the body, most experiments are done in vitro under conditions that the experimenter believes may be relevant. Once data is acquired, and there is some level of confidence in what the compound actually does, experiments with live patients or other organisms may be started. However, due to the complexity of a fully functioning host, the compound may interfere or react with pathways wholly unaccounted for in the in vitro trials. Even though two molecules appear to act on different biochemical pathways, it is possible that, in combination, they will wholly inhibit a completely different pathway, whereas, when alone, they would only inhibit one part of the pathway which the body could compensate for by using an alternate pathway. Thereby, the pathway in danger of being shut down would be undetected until the two drugs are used in conjunction.

Even with all the medication at our disposal, patients are fighting and living with cancer and other liver ailments, often for the rest of their lives. Often, the drugs are simply not effective enough to cure the cancer or the ailment completely and finding methods of combining drugs to increase effectiveness is extremely slow, costly, difficult, and often fruitless work.

Chinese Patent Application Publication No. 102225961A discloses a molecule comprising berberine and ursodeoxycholic acid with a linker of indeterminate length. This reference broadly states that the compound is useful for treating tumors, but this reference lacks instructive information or specific details that would be critical in determining the utility of the molecule, and a person of ordinary skill in the art would not reasonably consider this reference when designing molecules to combat specific forms of cancer due to its lack of information and data. Additionally, the tumors referenced could relate to non-cancerous tumors. The reference does not even provide any data that the disclosed molecule is, in fact, effective at anything it claims. The reference merely discloses generic molecules that may be used as carrier molecules. It is likely that even slightly different configurations of the molecule disclosed by the reference would have vastly different effects, or even no effects at all. Additionally, it is generally understood that a molecule can have vastly different effects on different medical conditions, even where the medical conditions appear to be somewhat related. Thus, even in light of this reference, a person of ordinary skill in the art would not be able to determine the usefulness, if any, of a molecule comprising berberine and ursodeoxycholic acid or effectively use any of the disclosed information to create liver cancer treatment methods.

Thus, there exists the need for effective methods and compounds for treating cancer and other liver ailments.

SUMMARY OF THE INVENTION

To minimize the limitations in the prior art, and to minimize other limitations that will become apparent upon reading and understanding the present specification, the present invention is directed to a compound and method of creating the compound for the treatment of liver cancer and other liver ailments.

One embodiment may comprise a method of treating cancer comprising the steps: identifying an individual having a cancer treatable by NAB03; administering said individual with an effective amount of NAB03:

DETAILED DESCRIPTION OF THE INVENTION

Figure 1:
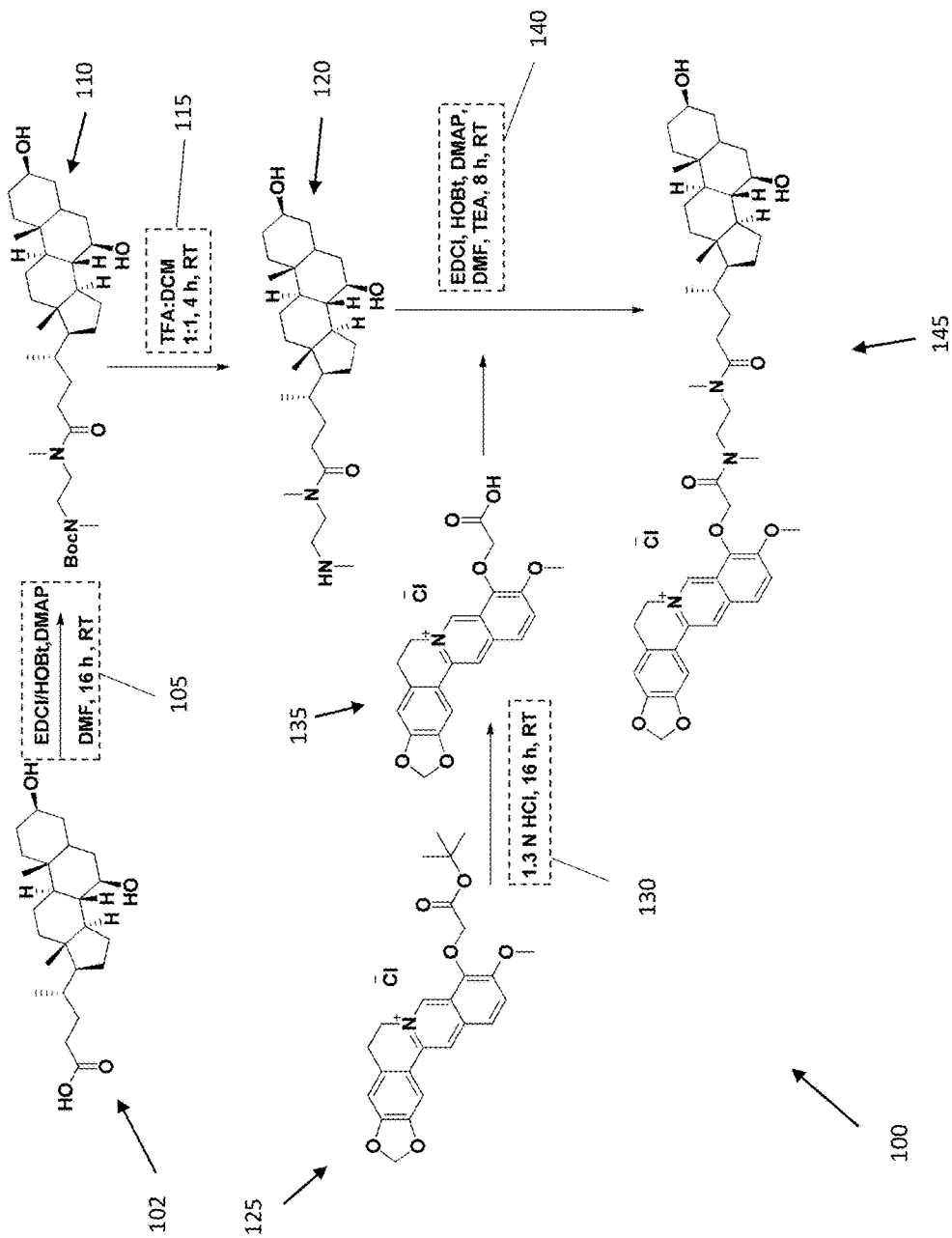
FIG. 1 is a flow diagram showing one method of synthesizing one embodiment of NAB03.

In the following detailed description of various embodiments of the invention, numerous specific details are set forth in order to provide a thorough understanding of various aspects of one or more embodiments of the invention. However, one or more embodiments of the invention may be practiced without some or all of these specific details. In other instances, well-known methods, procedures, and/or

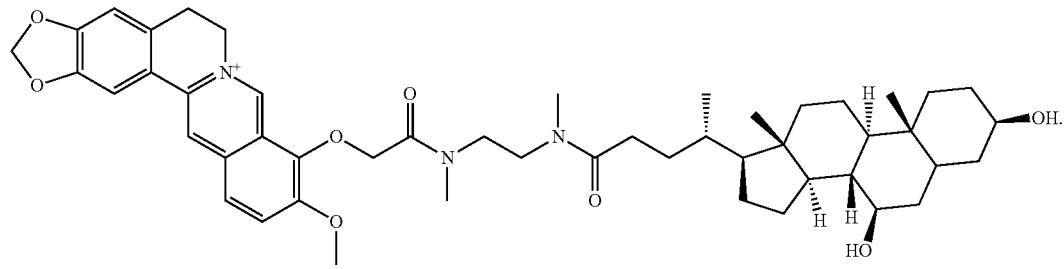 [SMILES: COc1ccc2cc3[n+](cc2c1OCC(=O)N(C)CCN(C)C(=O)CC[C@H](C)[C@@H]1CC[C@@H]2[C@H]4[C@H](O)CC5C[C@H](O)CC[C@@]5(C)[C@@H]4CC[C@]21C)CCc1cc2c(cc1-3)OCO2]

The cancer treatable by NAB03 may be a breast cancer. The cancer treatable by NAB03 may be a liver cancer. The cancer treatable by NAB03 may be a colorectal cancer. The cancer treatable by NAB03, when measured by CCK-8, may have an IC50 of less than 10 uM when exposed to NAB03 for more than 48 hours. The cancer treatable by NAB03 may, more specifically, be selected from the group consisting of the MDA468, PANC1, CCH, KMCH, Huh7, Huh2, and PC3 cell lines. The administering of the individual with the effective amount of NAB03 may be an oral administration. Alternatively, the administering of the individual with the effective amount of NAB03 may be an intravenous administration. The effective amount of NAB03 may be between approximately 2 mg per kg of said individual and approximately 6 mg per kg of said individual. Alternatively, the effective amount of NAB03 may be approximately 4 mg per kg of said individual.

Additional embodiments of the invention will be understood from the detailed description of the invention, by a person of ordinary skill in the art.

components have not been described in detail so as not to unnecessarily obscure aspects of embodiments of the invention.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the figures, and the detailed descriptions thereof, are to be regarded as illustrative in nature and not restrictive. Also, the reference or non-reference to a particular embodiment of the invention shall not be interpreted to limit the scope of the invention.

The present invention is aimed at increasing the life expectancy and quality of life of people with liver cancers, other liver ailments, and other cancers. The compound may selectively target certain liver cancers, effectively decreasing the required dosage of therapeutic drugs and increasing effectiveness. This also means that higher, potentially dangerous dosages may not be required.

In one embodiment of the present invention, the primary components of the compound are berberine and ursodeoxycholic acid and an amide linker. The compound, is suitably referred to as NAB03 hereinafter. In the following molecular structures, standard methods of representing molecular structures are used. Intersections of lines and endpoints of lines represent the presence of a carbon atom. When there is a letter at the end of a line, the element represented by that letter is present, instead of a carbon. Each line represents a bond. A floating line next to a line represents a double bond. A "+" symbol represents a positive charge. A "−" symbol represents a negative charge. C represents carbon, O represents oxygen, N represents nitrogen, H represents hydrogen, Cl represents Chlorine, Hg represents mercury, Br represents Bromine, Me represents methane or a single carbon with attached hydrogens, Boc represents a tert-butyloxycarbonyl protecting group, and R is a functional group which is variable. Dashed and bold lines represent orientation of the chemical bond, whether the bond is out of the plane or into the plane. Where a carbon is represented, but does not have a total of four bonds, hydrogens are present, as is the standard practice in drawing molecular structures. Arrows are used to indicate the order of reaction. Floating dots are used to represent electrons.

Berberine is a quaternary ammonium salt with a strong yellow coloring and is often found in plants and may have the structure:

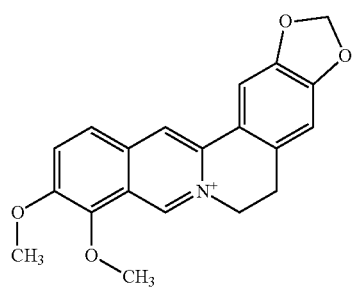 [SMILES: COc1ccc2cc3[n+](cc2c1OC)CCc1cc2c(cc1-3)OCO2]

Berberine was traditionally used as a dietary supplement and has some activity as an anti-fungal agent. Additionally, berberine has been shown to have some antibiotic effect when used in combination with other molecules, such as methoxyhydnocarpin. There is some evidence that berberine is effective in treating trachoma. Berberine is also used to treat leishmaniasis. Berberine is believed to suppress proinflammatory cytokines and E-selectin. Importantly, berberine is a nucleic acid-binding isoquinolone alkaloid with wide potential therapeutic properties.

There are also many new experimental uses of berberine which implicate berberine's use in treating a wide array of ailments, including, but not limited to: diabetes mellitus; high cholesterol; nonalcoholic fatty liver disease; cardiovascular conditions; transplant rejections; cancer; depression; intestinal disorders; and human immunodeficiency virus. One proposed method of how berberine treats cancer is by berberine's ability to inhibit angiogenesis and to modulate Mcl-1, Bcl-xL, cyclooxygenase (COX)-2, MDR, tumor necrosis factor (TNF)- and IL-6, iNOS, IL-12, intercellular adhesion molecule-1 and ELAM-1 expression, MCP-1 and CINC-1, cyclin D1, activator protein (AP-1), HIF-1, PPAR-, and topoisomerase II.

The features of berberine that may be utilized by the current invention are its anti-cancer properties and anti-liver ailment properties.

Ursodeoxycholic acid is a secondary bile acid synthesized by the liver and has the structure:

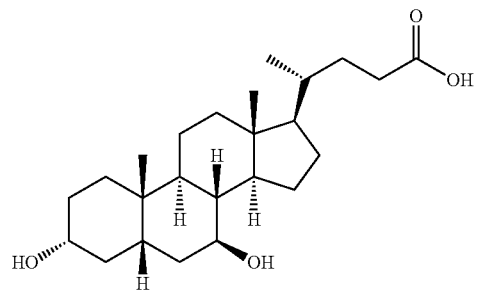

Ursodeoxycholic acid, also known as ursodiol, shows organotropism for the hepatoportal circuit. Because of this, ursodeoxycholic acid may be used to introduce molecules to the liver and the liver's pathways. Ursodeoxycholic acid is primarily used by the body to help digest fats and to regulate cholesterol by reducing the rate at which the intestine absorbs cholesterol molecules while breaking up micelles containing cholesterol. This feature of ursodeoxycholic acid is also helpful in patients with gallstones that would like an alternative to surgery. Ursodeoxycholic acid is also currently the only FDA approved drug for the treatment of primary biliary cirrhosis. However, because of ursodeoxycholic acid's effects in inhibiting apoptosis, it is not thought of to be used in the treatment of cancer which often features inducing apoptosis of cancer cells.

Berberine and ursodeoxycholic acid may be combined by preparing each molecule by adding desired functional groups. Once the desired functional groups are added, the berberine and ursodeoxycholic acid may be combined.

Various chemicals may be used in order to combine berberine and ursodeoxycholic acid. Some solvents comprise: DMF; diethyl ether; MeOH; CHCl3; DCC; TFA; TEA; and DMP. Additionally, several reagents may be used to directly modify and add onto berberine and its intermediaries in order to create NAB03. Furthermore, neutral alumina columns and thin layer chromatography plates may be used to purify and concentrate desired molecules at various stages of the synthesizing process. Additional methods may be used to purify and concentrate the desired products. Substitutions of the various solvents, reagents, and catalysts may be used. Often, these substitutions may be of a similar family or possess similar characteristics.

DMF is a polar aprotic solvent with a high boiling point and has the molecular structure:

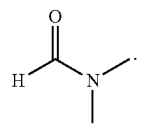

DMF is typically colorless and miscible with water and commonly used as a solvent for chemical reactions. DMF is short for dimethylformamide.

Diethyl ether is an organic compound in the ether class and has the following molecular structure:

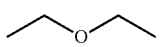

Diethyl ether is typically colorless and is a highly volatile flammable liquid. It is commonly used as a solvent and was once used as an anaesthetic. Since its original discovery and use, it has been discovered that diethyl ether has narcotic properties and its use may lead to addiction, known as etheromania.

MeOH is an organic compound in the alcohol class and has the following molecular structure:

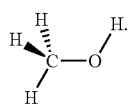

MeOH is typical colorless and is the simplest alcohol. MeOH is short for methanol. It is light, volatile, and flammable, similar to ethanol. MeOH is a polar liquid and often used as a solvent.

CHCl3 is a chloromethane commonly known as chloroform and has the following molecular structure:

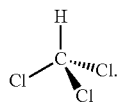

CHCl3 is an organic compound, sweet smelling and fairly dense. CHCl3 is also somewhat hazardous and is often portrayed as a chemical used in order to render a person unconscious. Additionally, CHCl3 may be fatal if too much is used which is one of the reasons CHCl3 fell out of favor as use as an anaesthetic.

DCC is an organic compound and has the following molecular structure:

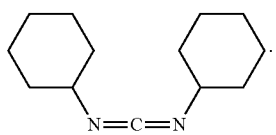

DCC is often a white crystal with a sweet odor and is commonly used to couple amino acids in artificial peptide synthesis. DCC is short for N—N'-dicyclohexylcarbodiimide. One possible mechanism for DCC used in the present invention is that DCC may activate the terminal OH in the carboxyl group of the ursodeoxycholic acid 145, allowing for the terminal amine of the berberrubine-9-hexyl amine 140 to attack the carbon on the hydroxyl group of the ursodeoxycholic acid 145, as shown in FIG. 1, discussed below.

DMP is a derivative of pyridine and has the following molecular structure:

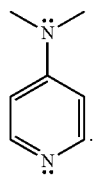

DMP is often a colorless solid and useful as a nucleophilic catalyst. DMP is short for 4-dimethylaminopyridine. DMP's catalytic function is often used as an acyl transfer catalyst in conjunction with DCC, commonly known as a Steglich esterification.

EDCl is 1-Ethyl-3-(3-dimethylaminopropyl)carbodiimide and has the following molecular structure:

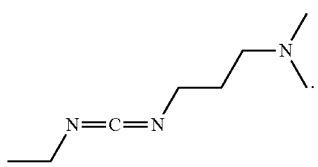

EDCl is a water-soluble carbodiimide usually obtained as the hydrochloride. It is typically employed in the 4.0-6.0 pH range. It is generally used as a carboxyl activating agent for the coupling of primary amines to yield amide bonds. Additionally, EDCl can also be used to activate phosphate groups in order to form phosphomono-esters and phosphodi-esters.

HOBt is Hydroxybenzotriazole, and has the following structure:

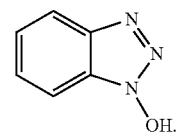

HOBt is an organic compound that is a derivative of benzotriazole. HOBt is mainly used to suppress the racemization of single-enantiomer chiral molecules and to improve the efficiency of peptide synthesis.

TFA is Trifluoroacetic acid and is an organofluorine compound with the chemical formula CF3CO2H.

TEA is trimethylamine and is a volatile liquid commonly used in organic synthesis with the chemical formula N(CH2CH3)3.

The Steglich esterification process allows for the formation of esters under relatively mild conditions. First DCC activates the carboxyl acid, and then DMP acts as an acyl transfer catalyst as follows:

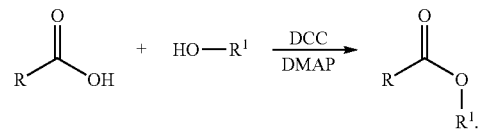

When the Steglich esterification process is used with an amine, the reaction occurs as follows:

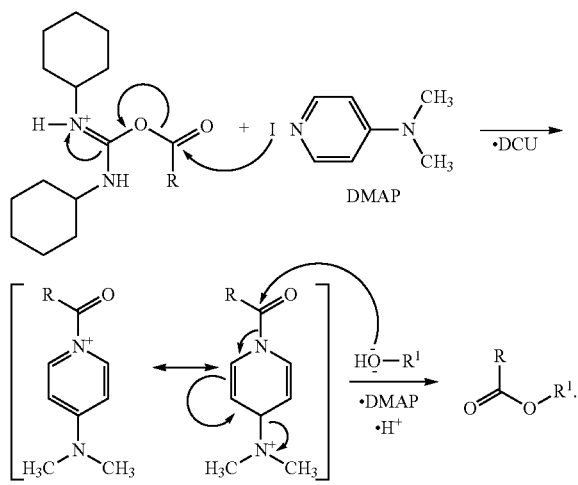

If the Steglich esterification process is used with an amine and proceeds at a relatively slow rate, a side-reaction with an undesirable side-product may occur. This side reaction is a 1,3-rearrangment of the O-acyl intermediate to an N-acyl urea which is unable to further react with an alcohol. The second reaction occurs when the Steglich esterification process proceeds at a relatively slow rate.

NAB01 refers to a molecule with a molecular structure as follows:

NAB03 refers to a molecule with a molecular structure as follows:

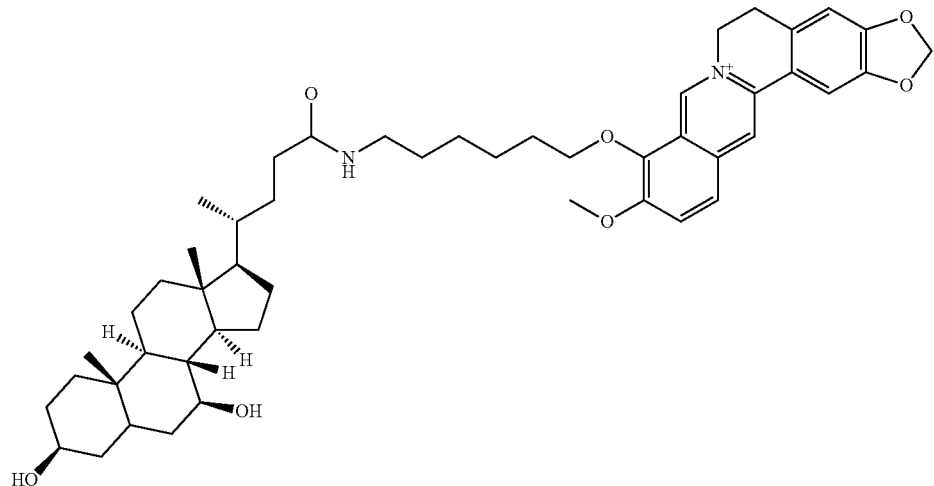 [SMILES: COc1ccc2cc3[n+](cc2c1OCCCCCCNC(O)CC[C@@H](C)[C@H]1CC[C@H]2[C@@H]4[C@@H](O)CC5C[C@@H](O)CC[C@]5(C)[C@H]4CC[C@]12C)CCc1cc2c(cc1-3)OCO2]

embodiment of the method of synthesizing NAB03 102 preferably comprises starting with two reactions in parallel, the first urso reaction 105 begins with ursodeoxycholic acid 102, and the first berb reaction 130 begins with berberine 125. Each of the ursodeoxycholic acid 102 and the berberine 125 may be modified through chemical reactions until the products of the chemical reactions are reacted with one another, producing NAB03 145. One key component of NAB03 145 is that NAB03 145 comprises an amide linker between its ursodeoxycholic acid 102 portion and the berberine 125 portions.

The first urso reaction 105 may comprise reacting the ursodeoxycholic acid 102 with EDCl, HOBt, DMAP, in a DMF solvent, for about 16 hours, at approximately room temperature to add an amid linker, which is protected by a tert-Butyloxycarbonyl protecting group ("Boc"). Room temperature, as used herein, is generally 20° C. to 27° C., and more specifically, about 25° C. The reaction product of the first urso reaction 105 may be the first urso reaction product 110. The first urso reaction product 110 may then undergo a second urso reaction 115, wherein the first urso reaction product 110 may react with a TFA:DCM solvent/reactant having a ratio of 1TFA:1DCM by volume, for about 4 hours, at about room temperature. The reaction product of the second urso reaction 115 may be a second urso reaction product 120.

The first berb reaction 130 may comprise reacting the berberine 125 in an about 1.3N HCl solution for about 15 hours. The reaction product of the first berb reaction 130 may be a first berb reaction product 135, wherein a C4 group on the end of the berberine 125 is removed.

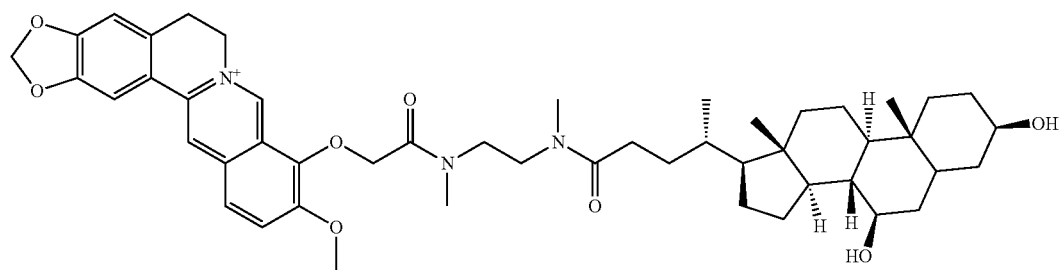 [SMILES: COc1ccc2cc3[n+](cc2c1OCC(=O)N(C)CCN(C)C(=O)CC[C@H](C)[C@@H]1CC[C@@H]2[C@H]4[C@H](O)CC5C[C@H](O)CC[C@@]5(C)[C@@H]4CC[C@]21C)CCc1cc2c(cc1-3)OCO2]

FIG. 1 is a flow diagram showing one method of synthesizing one embodiment of NAB03. As shown in FIG. 1, one The first berb reaction product 135 and the second urso reaction product 120 may then undergo a berb-urso reaction 140. The berb-urso reaction 140 may comprise reacting the second urso reaction product 110 and first berb reaction product 135 with EDCl, HOBt, DMAP, and TEA in a DMF solvent for about 8 hours at about room temperature. The reaction product of the ber-urso reaction 140 may be a berb-urso product 145, which may also be referred to as NAB03. The berb-urso product 145 may be desired endpoint of the method of synthesizing NAB03 100.

In one embodiment, the berberine 125 may be prepared by dissolving Berberrubine A (about 1 g, 2.80 mmol) in 12 ML of DMF, wherein this mixture may then added to Tert-butyl bromoacetate (about 650 mg, 3.3 mmol) at room temperature. This reaction mixture may then be heated to about 65° C. for 3 hours. After the reaction is completed, the reaction mixture may be cooled to room temperature and precipitated with diethyl ether. The product of this precipitation may be purified by column chromatography utilizing a neutral-aluminium oxide with an eluent of 1-2% methanol in DCM to produce about 600 mg of the berberine 125.

Once the berberine 125 is prepared, about 600 mg of berberine 125 may be suspended in a THF:MeOH (about 1:1) mixed solution. To this suspended solution, 1.3 N HCL may be added and stirred for 6 hours at room temperature. Once the reaction is completed, the product of the reaction may be purified by column chromatography utilizing neutral aluminum oxide and an eluent of about 5-8% MeOH in DCM to get about 280 g of the first berb reaction product 135.

The ursodeoxycholic acid 102 (about 300 mg, 0.765 mmol) may be suspended in about 5 mL of DMF. The suspension may be cooled to 0° C., and then N,N'-dimethyl monoboc (about 143.8 mg, 0.765 mmol), DMAP (about 140 mg, 1.147 mmol), HOBT (about 154.9 mg, 1.147 mmol), and EDCl (about 219 mg, 1.147 mmol) may be added to the DMF and ursodeoxycholic acid 102 solution. The reaction mixture may then be brought to room temperature and stirred for about 16 hours. Once the reaction is completed, the reaction mass may be diluted with ethyl acetate and washed with water. The organic layer may then be dried and concentrated. Then, reaction products may be purified by column chromatography using silica gel 100-200Mesh, and an eluent of about 2-3% MeoH:DCM to produce about 400 mg of the first urso reaction product 105.

Then, the first urso reaction product (about 50 mg, 0.088 mmol) may be suspended in about 1.5 mL of DCM and 1.5 mL of Trifluro acetic acid at room temperature and stirred for about 5 hours. Once the reaction is completed, the second urso reaction product 120 may be produced, and the second urso reaction product 120 need not undergo purification before the next step.

The second urso reaction product 120 (50 mg, 0.108 mmol) and the first berb reaction product 135 (41 mg, 0.108 mmol) may be suspended in 2 mL of DMF and cooled to 0° C. Then, DMP (20 mg, 0.162 mmol) and HOBT (21 mg, 0.162 mmol) may be added, followed by the addition of EDCl (30 mg, 0.162 mmol) and TEA (13.1 mg, 0.129 mmol). The reaction mixture may then be stirred for 16 hours at room temperature. Diethyl ether may then be used to precipitate the reaction products, which may then be purified by prep TLC, an eluent of 3% MeOH in DCM to produce about 90 mg of the berb-urso product 145 known as NAB03.

Figure 2:
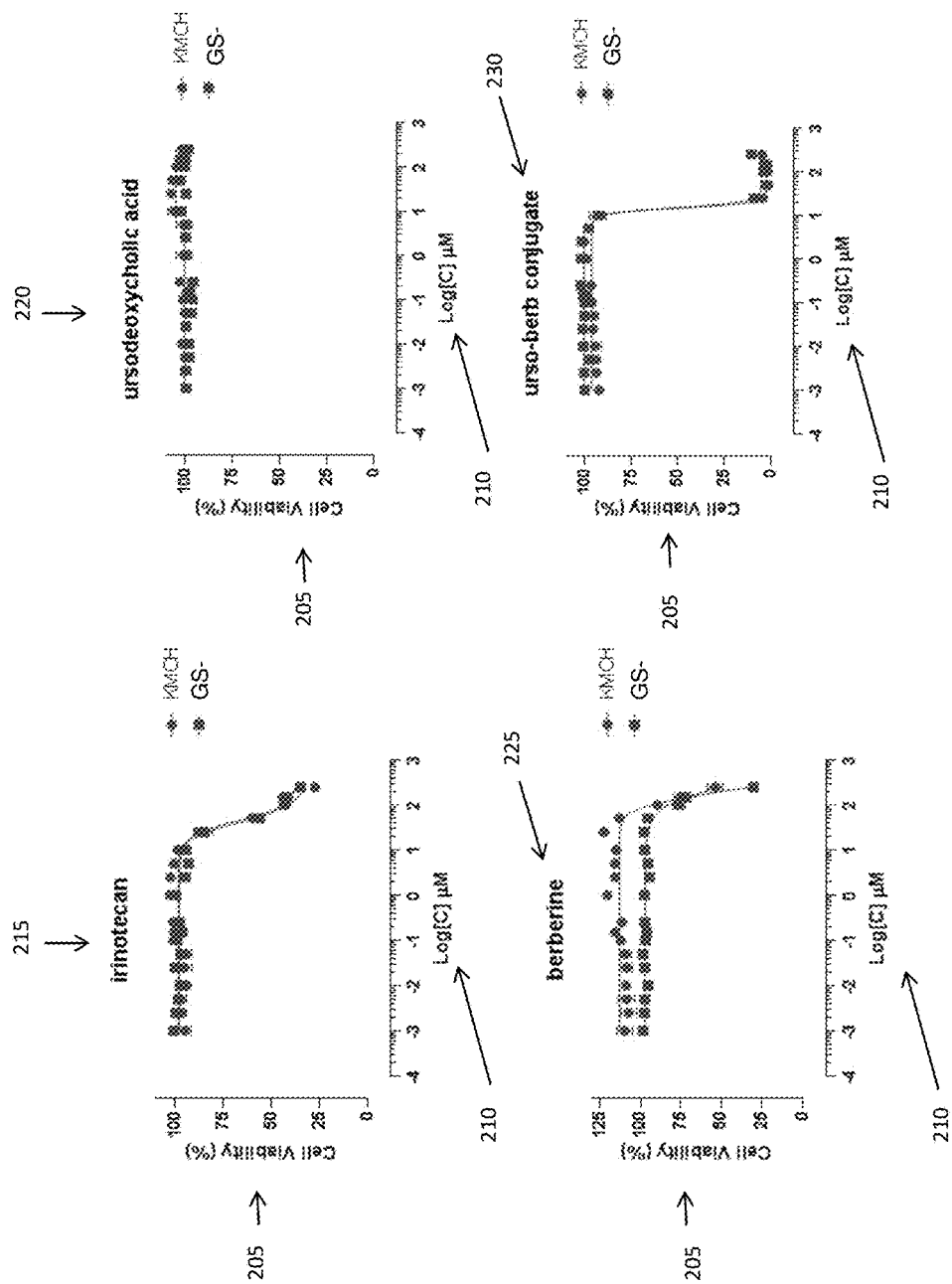
FIG. 2 is a set of graphs showing the ability of various molecules to kill KMCH and GS-Li013 cells, which are cholangiocarcinoma cells.

FIG. 2 is a set of graphs showing the ability of various molecules to kill KMCH and GS-Li013 cells, which are cholangiocarcinoma cells. The data presented in FIG. 2 is based on in-vitro studies. The y-axis of each graph represents the Cell viability percentage 205 of KMCH and GS-Li013 cells. The x-axis of each graph represents the Log [C] 210. [C] refers to the concentration of the molecule tested in uM. IC50 commonly refers to the half maximal inhibitory concentration, and is used to numerically represent the efficacy of various molecules to be effective in their respective tasks. In this case, IC50 means the concentration at which half of the target cells are no longer viable. Thus, the lower the IC50 value is, the more effective the molecule is in accomplishing what is being measured, in this case, killing cholangiocarcinoma cells. The unit uM is used to represent the IC50 value. uM is the same as micro molar concentration, which is $10^{-6}$ moles/liter, a common concentration unit.

As shown in FIG. 2, the IC50 of four molecules were determined over a 24-hour period treatment. The first molecule, irinotecan, shown in the irinotecan graph 215, is a known chemotherapy drug used on cholangiocarcinoma cells, and has an IC50 of 90 uM when used on GS– cell lines and an IC50 of 95 uM when used on KMCH cell lines. The second molecule, ursodeoxycholic acid, shown in the ursodeoxycholic acid graph 220, may be a primary component in NAB01 and NAB03, is not cytotoxic on its own, and accordingly, as shown, has no IC50 on both KMCH and GS– cell lines. The third molecule, berberine, shown in the berberine graph 225, may be a primary component in NAB01 and NAB03, and has an IC50 of 200 uM on both KMCH and GS– cell lines. This shows that berberine has some cytotoxic ability, but is not as effective as irinotecan. The fourth molecule, an urso-berb conjugate, which as used herein refers to the molecule NAB01, shown in the urso-berb graph 230, has an IC50 of 15 uM on both KMCH and GS– cell lines. The IC50 of NAB01 is much lower than berberine, the main cytotoxic component, and the IC50 of NAB01 is even lower than irinotecan. Thus, the combination of two relatively ineffective molecules is able to be more effective than the known and used molecule irinotecan. Thus, this data shows that the IC50 of NAB01 is much lower than one would expect, and shows an unexpectedly high effectiveness of NAB01 on certain cancerous cell lines. Furthermore, the IC50 of NAB01 is still higher than the IC50 of NAB03 with respect to KMCH, as shown below in FIG. 9. Accordingly, while the combination of berberine and ursodeoxycholic acid (NAB01) was unexpectedly effective at treating KMCH, the combination of berberine and ursodeoxycholic acid linked by an amide linker (NAB03) is even more effective than what was previously considered unexpectedly effective. Additionally, as explained hereinbelow, NAB03 and NAB01 have drastically different levels of efficacy on different cancerous cell lines.

To obtain the data in FIG. 2, and the other IC50 data hereinbelow, Cell Counting Kit-8 (CCK-8) was used. CCK-8 is commercially available from Dojindo Molecular Technologies, Inc. CCK-8 allows sensitive colorimetric assays for the determination of cell viability in cell proliferation and cytotoxicity assays. Dojindo's highly water-soluble tetrazolium salt, used in CCK-8, is reduced by dehydrogenase activities in cells to give a yellow-color formazan dye, which is soluble in the tissue culture media. The amount of the formazan dye, generated by the activities of dehydrogenases in cells, is directly proportional to the number of living cells. The detection sensitivity of CCK-8 may be higher than the other tetrazolium salts such as MTT, XTT, MTS or WST-1. Cancerous cells in a cell culture were exposed to the either irinotecan, ursodeoxycholic acid, berberine, or NAB01, and the results were recorded. Various concentrations of each molecule were used, resulting in different amount of cell viability. Cell viability was measured according to the procedures of CCK-8, namely higher cell counts lead to higher absorption measurements, which would mean lower drug efficacy. Although CCK-8 was used herein, it is understood that suitable cell counting methods may be used.

Figure 3:
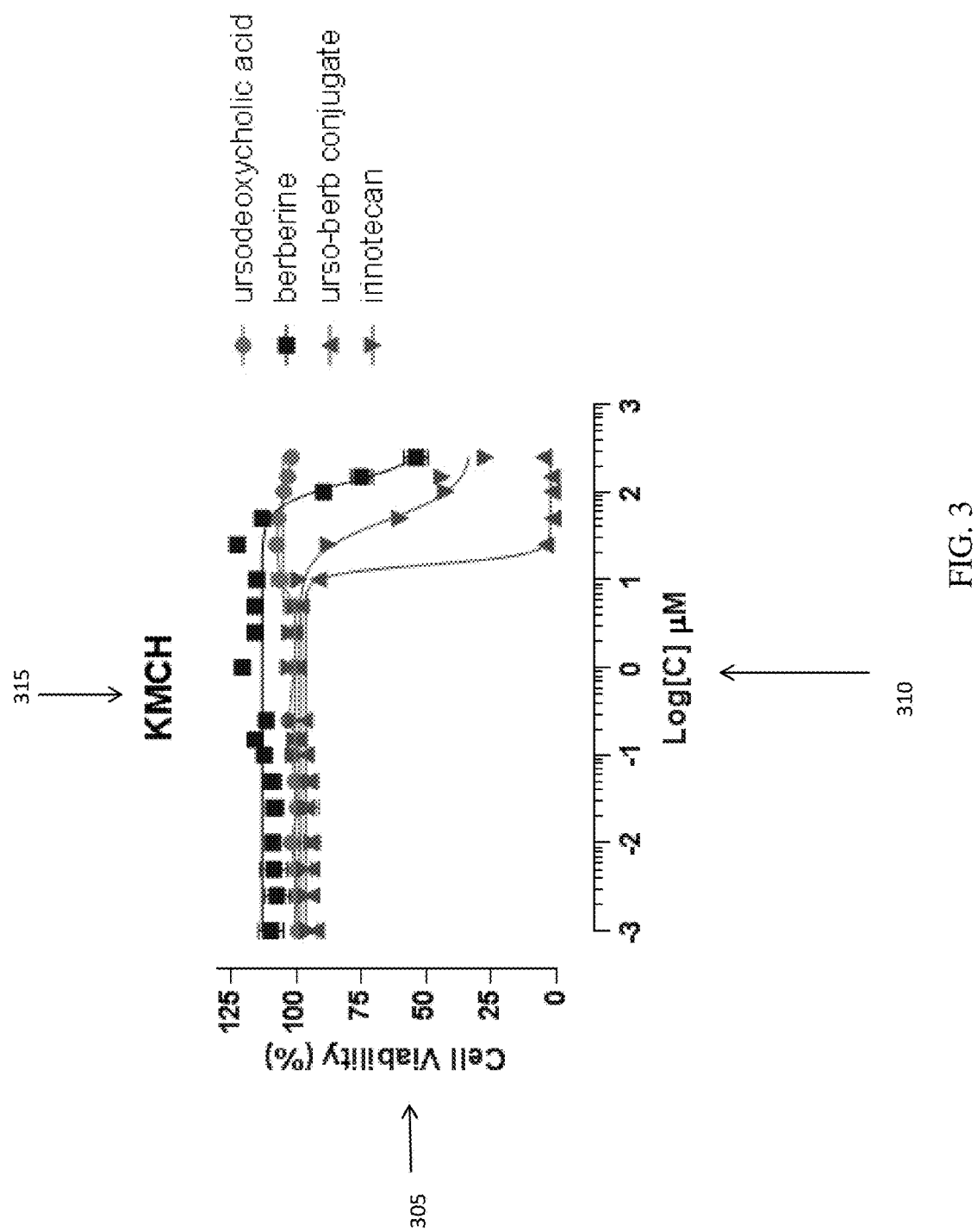
FIG. 3 is a graph that overlays data showing the IC50 of various molecules with KMCH cells.

FIG. 3 is a graph that overlays data showing the IC50 of various molecules with KMCH cells. As shown in FIG. 3, a KMCH graph 315 has a y-axis showing cell viability percentage 305 of KMCH cells and an x-axis showing the Log [C] 310. [C] refers to the concentration of the various molecules tested in uM. The data presented in FIG. 3 is based on in-vitro studies. As visually depicted in FIG. 3, the IC50 of NAB01 is significantly lower than either of NAB01's components, berberine and ursodeoxycholic acid, when used on KMCH cell lines. Additionally, the IC50 of NAB01 is significantly lower than irinotecan, a known chemotherapy drug. Furthermore, NAB03 has an even lower IC50 than NAB01, as shown below.

Figure 4:
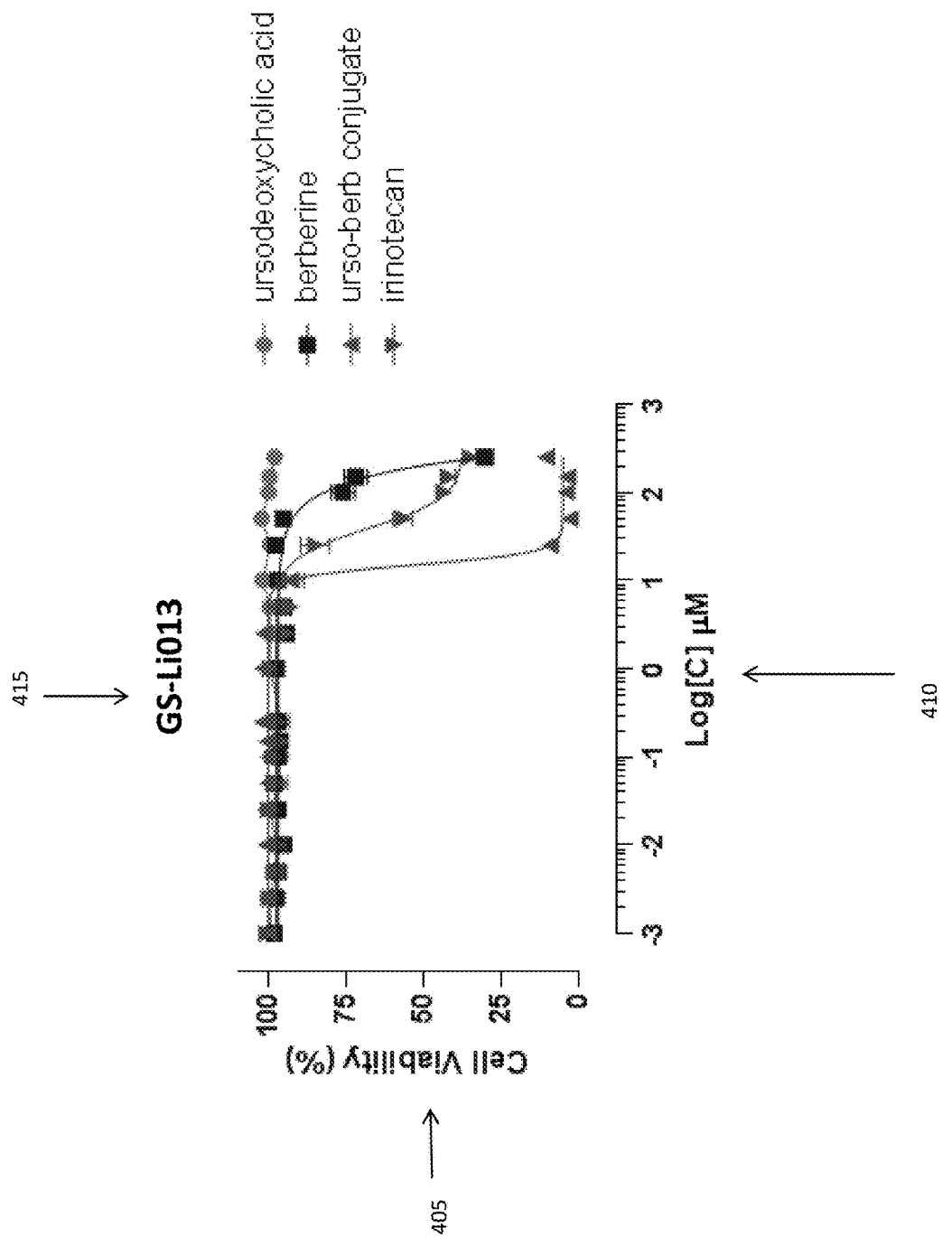
FIG. 4 is a graph that overlays data showing the IC50 of various molecules in GS-LI013 cells.

FIG. 4 is a graph that overlays data showing the IC50 of various molecules in GS-LI013 cells. As shown in FIG. 4, a GS-LI013 graph 415 has a y-axis showing cell viability percentage 405 of GS-LI013 cells and an x-axis showing Log [C] 410. [C] refers to the concentration of the various molecules tested in uM. The data presented in FIG. 4 is based on in-vitro studies. As visually depicted in FIG. 4, the IC50 of NAB01 in GS-LI013 cells is significantly lower than either of NAB01's components, berberine and ursodeoxycholic acid, when used on GS-LI013 cell lines. Additionally, the IC50 of NAB01 is significantly lower than irinotecan, a known chemotherapy drug, in GS-LI013 cells.

Figure 5:
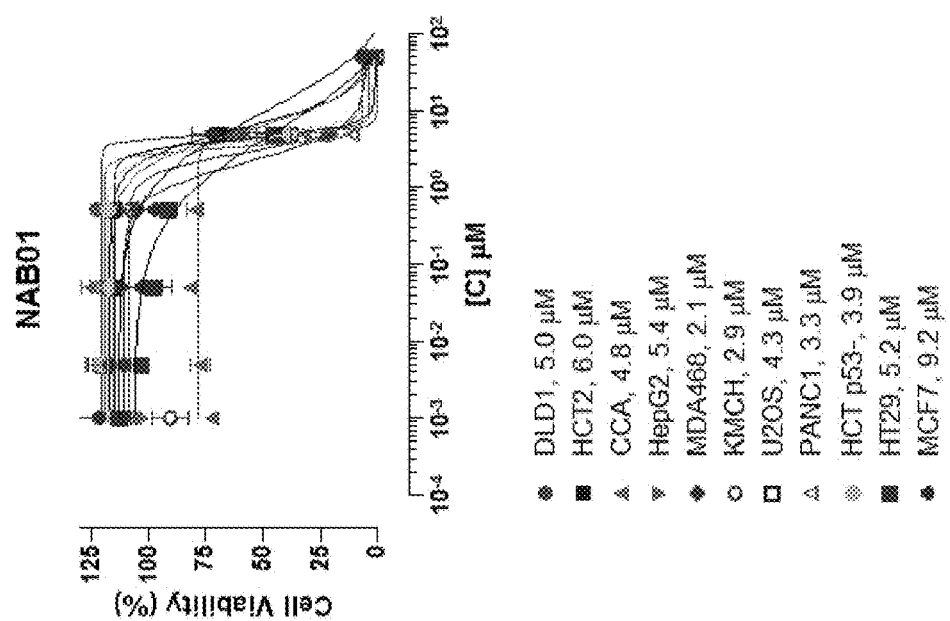
FIG. 5 is a graph that overlays data showing the IC50 of NAB01 with various cancerous cell lines over a 48-hour period.

FIG. 5 is a graph that overlays data showing the IC50 of NAB01 with various cancerous cell lines over a 48-hour period. As shown in FIG. 5, NAB01 has an unusually high efficacy on several cell lines, with an IC50 of less than 10 uM as measured through CCK-8 methodology, described above. DLD1 refers to Dukes' type C, colorectal adenocarcinoma, and NAB01 has an IC50 of 5.0 uM for DLD1. HCT2 refers to a hamster lymphoid cell line, and NAB01 has an IC50 of 6.0 uM for HCT2. CCA refers to a cholangiocarcinoma cell line, and NAB01 has an IC50 of 4.8 uM for CCA. HepG2 refers to a hepatocellular carcinoma cell line, and NAB01 has an IC50 of 5.4 uM for HepG2. MDA468, also known as MDA-MB468, refers to a triple negative adenocarcinoma cell line of the breast, and NAB01 has an IC50 of 2.1 uM for MDA468. KMCH refers to a hepatocellular and cholangiocarcinoma cell line, and NAB01 has an IC50 of 2.9 uM for KMCH. U2OS refers to a sarcoma of the tibia cell line, and NAB01 has an IC50 of 4.3 uM for U2OS. PANC1 refers to an epithelioid carcinoma cell line, and NAB01 has an IC50 of 3.3 uM for PANC1. HCT refers to a colorectal carcinoma cell line, and NAB01 has an IC50 of 3.9 uM for HCT. HT29 refers to a colorectal adenocarcinoma cell line, and NAB01 has an IC50 of 5.2 uM for HT29. MCF7 is an adenocarcinoma cell line of the breast, and NAB01 has an IC50 of 9.2 uM. NAB01 has an unexpectedly effective IC50 of less than 10 uM for the cell lines described above, and the related cancers.

Figure 6:
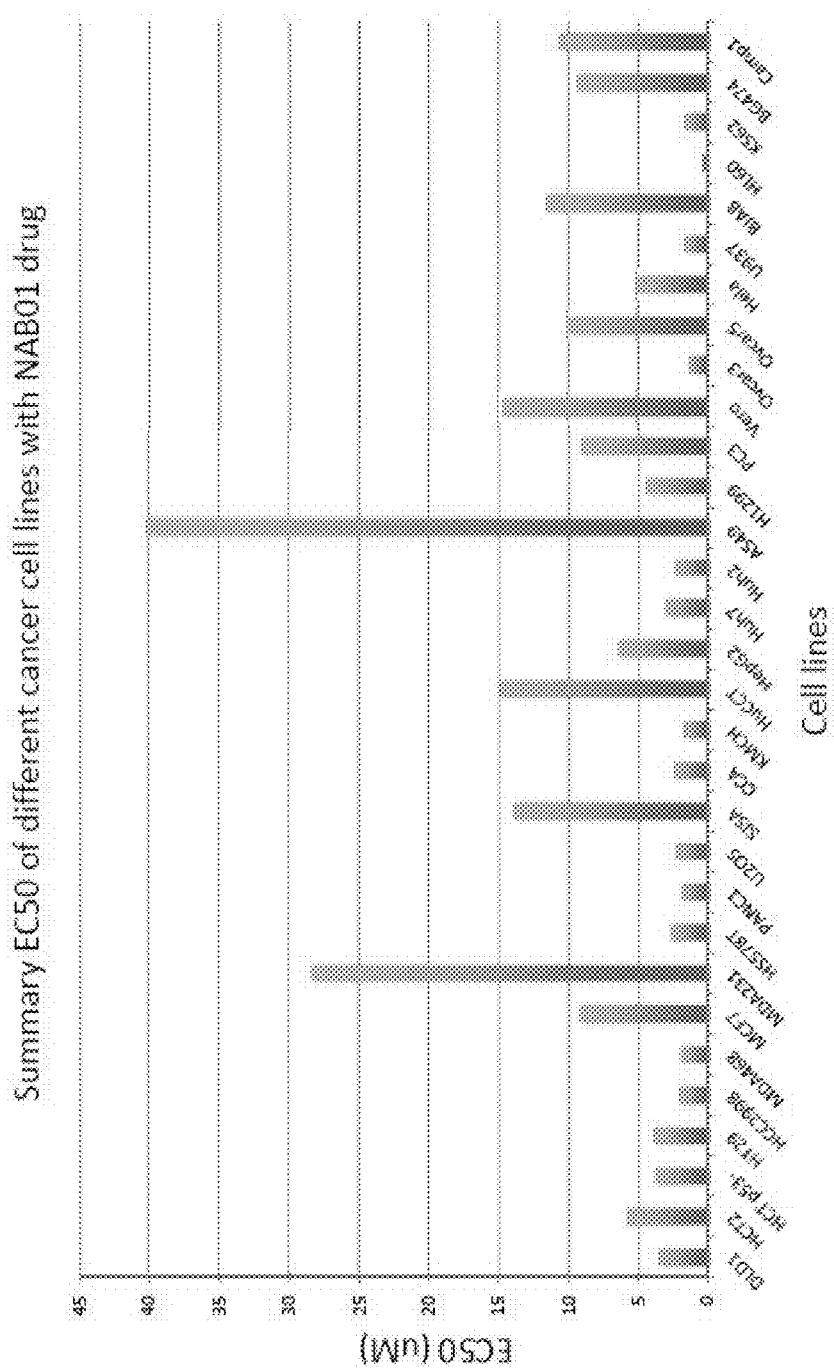
FIG. 6 is a bar graph that shows the efficacy of NAB01 in terms of IC50 of NAB01 with various cancerous cell lines over a 48-hour period.

FIG. 6 is a bar graph that shows the efficacy of NAB01 in terms of IC50 of NAB01 with various cancerous cell lines over a 48-hour period. As shown in FIG. 6, the cancerous cell lines, when treated with NAB01 that had IC50 of more than 10 uM comprise: MDA231, SJSA, HuCCT, A549, Vero, BJAB, and Camp1. The cancerous cell line, when treated with NAB01 that had an IC50 of 10 was Ovcar5. The cancerous cell lines, when treated with NAB01 that had an IC50 of less than 10 uM were DLD1, HCT2, HCT p53, HT29, HCC2998, MDA468, MCF7, HS578T, PANC1, U2OS, CCA, KMCH, HepG2, Huh7, Huh2, H1299, PC3, Ovcar3, Hela, U937, HL60, K562, BG474.

Figure 7:
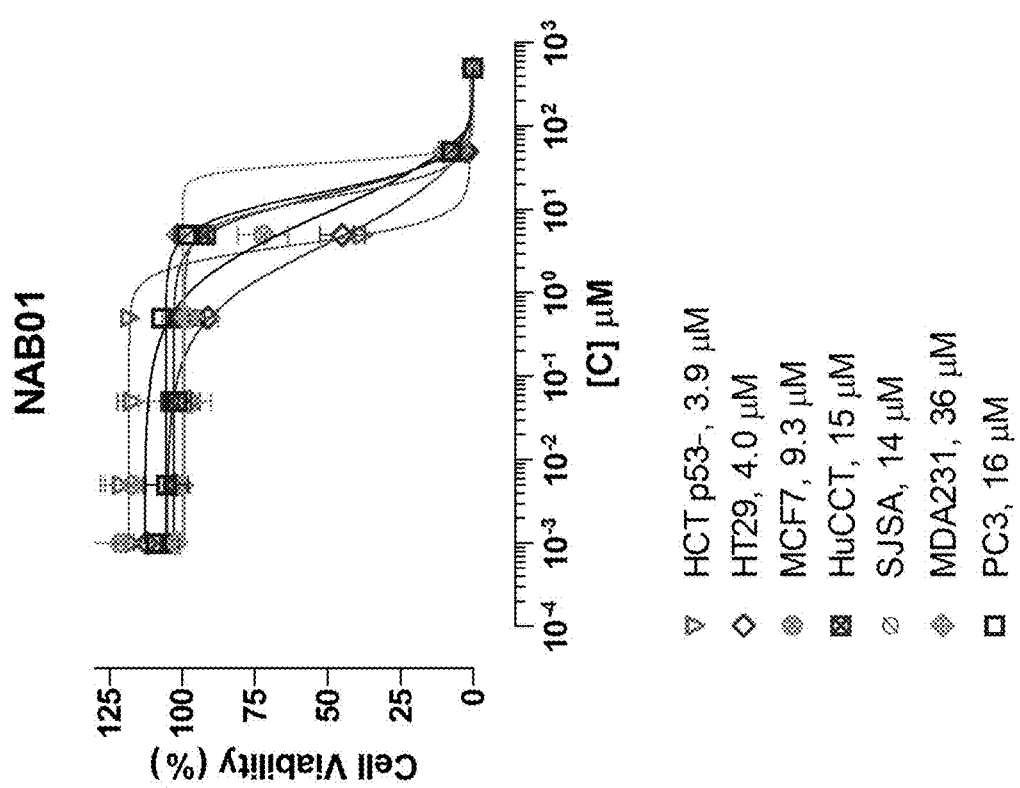
FIGS. 7-8 show the efficacy of NAB01 on various cancerous cell lines.
Figure 8:
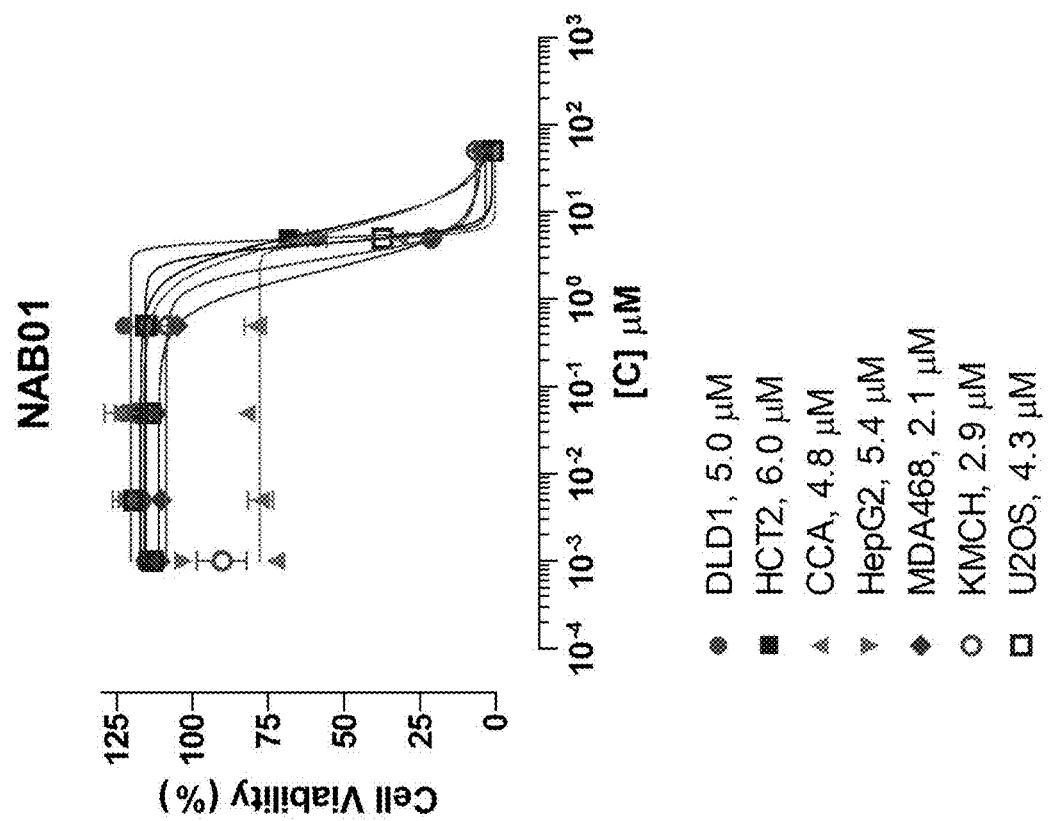

FIGS. 7-8 show the efficacy of NAB01 on various cancerous cell lines. As shown in FIGS. 7-8, the efficacy of NAB01 can vary greatly depending on the cancerous cell line, and as a result, NAB01 may not be effective against certain cell lines. The data reflected in FIGS. 19-20 was collected over a 48-hour period, under the same conditions as the data shown in FIG. 5. When NAB01 has an IC50 of greater than approximately 10 uM, it can generally said to be less effective, and the higher than IC50 value, the less effective NAB01 is for that particular cell line. NAB01 can be considered effective for cell lines when its IC50, as measured under the present conditions and methods, is approximately 10 uM or lower. For example, NAB01 is not particularly effective on SJSA, HuCCT, PC3, and MDA231 cell lines. NAB01 has an IC50 of 14 uM for SJSA, 15 uM for HuCCT, 16 uM for PC3, and 36 uM for MDA231. Accordingly, the determination of for which cancer types are treatable by NAB01 is limited, and in order to determine which cancer types are treatable requires extensive research.

Figure 9:
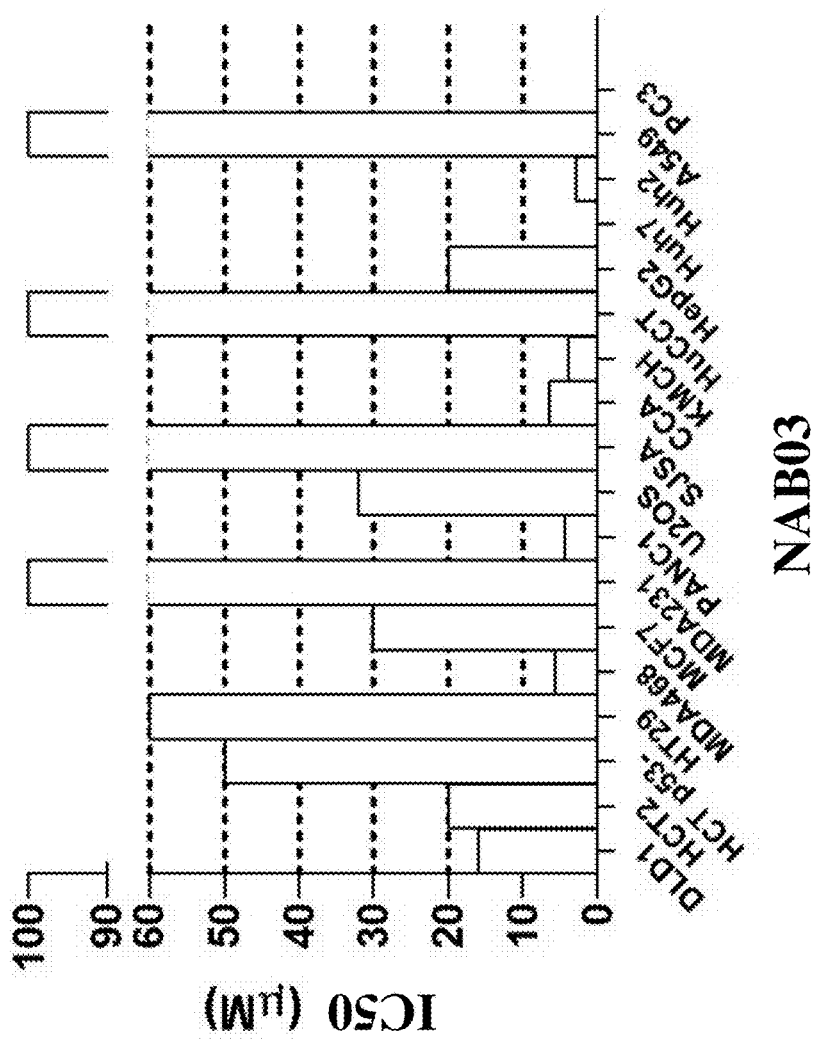
FIG. 9 is a bar graph that shows the efficacy of NAB03 molecules in rendering various cancerous cell lines non-viable.

FIG. 9 is a bar graph that shows the efficacy of NAB03 molecules in rendering various cancerous cell lines non-viable. The data presented in FIG. 9 is based on in-vitro studies. The y-axis of the graph represents the IC50 value of NAB03 with respect to various cancerous cell lines. The x-axis of the graph represents various cancerous cell lines. As shown in FIG. 9, NAB03 is unusually effective on certain cancerous cell lines, and ineffective on certain other cancerous cell lines. Importantly, while NAB03 is somewhat similar in structure to NAB01, NAB03's efficacy profile is drastically, and unexpectedly, different.

The term "highly effective" as used herein means having an IC50 low enough for NAB03 to be considered a reasonable option for treating the cancer type to which the cancerous cell line corresponds. A "highly effective" IC50 is generally less than about 10 uM, as used herein.

As shown in FIG. 9, NAB03 may be highly effective and have an IC50 of less than 10 uM on cancerous cell lines MDA468, PANC1, CCH, KMCH, Huh7, Huh2, and PC3. As shown in FIG. 9, NAB03 may be not very effective, having an IC50 of between 10 and 60 for the cancerous cell lines HCT2, HCT p53, HT29, MCF7, U2OS, and HepG2. Also as shown in FIG. 9, NAB03 may be not effective, having an IC50 of over 60 uM for the cancerous cell lines MDA231, SJSA, HuCCT, and A549.

Importantly, as shown in FIG. 9, and as compared to FIG. 6, NAB03 has a very different efficacy profile as compared to NAB01 that could not be predicted without extensive experimentation. For example, whereas NAB03 is not very effective for cancer cell lines HCT2, HCT p53, HT29, MCF7, U2OS, and HepG2; NAB01 is highly effective, having an IC50 of less than 10 uM for cancer cell lines HCT2, HCT p53, HT29, MCF7, U2OS, and HepG2. Additionally, NAB03 is even more effective than NAB01 with respect to Huh7 and PC3. Accordingly, the determination of for which cancer types are treatable by NAB03 is limited, and in order to determine which cancer types are treatable requires extensive research.

As described above, ursodeoxycholic acid is useful in the therapy of liver cancer and other liver ailments, including liver cirrhosis, primary sclerosing, cholangitis, cholelithiasis, non-alcoholic fatty liver disease, and non-alcoholic steatohepatitis. Also, because ursodeoxycholic acid is naturally produced by intestinal bacteria as a byproduct of primary bile acids, it demonstrates organotropism in the hepatoportal circuit. Berberine is a DNA binding molecule with general anti-cancer properties. By attaching berberine to ursodeoxycholic acid, the resulting conjugate has an increased uptake in the hepatoportal circuit while binding to and fighting cancer cells. Because many cancer fighting treatments induce apoptosis in cancer cells, cancer fighting treatment compounds are not typically combined with a molecule like ursodeoxycholic acid, which is itself believed to prevent apoptosis. Thus, the combination of these two molecules in use together would not be expected or intuitive. NAB03 may be taken orally, and then enter the hepatoportal circuit through the same mechanisms as ursodeoxycholic acid would.

NAB03 may also be combined with traditional chemotherapy for liver cancer. NAB01 may target the hepatic portal circuit, in addition to the liver specifically. This hepatic portal circuit includes, but is not limited to, organs such as the liver, gall bladder, duodenum, and small intestine.

Details such as quantity of items used, volume of solutions, temperatures, reaction times, filtration details, and all other aspects of the reaction may be variable. Much larger scales of production may also be used with substantially similar but adapted methods. The quantities and figures described herein refer to one of a multitude of methods to prepare the invention and analogs of the invention.

What is claimed is:

1. A method of treating cancer comprising the steps:
identifying an individual having a cancer treatable by NAB03;
administering said individual with an effective amount of NAB03:

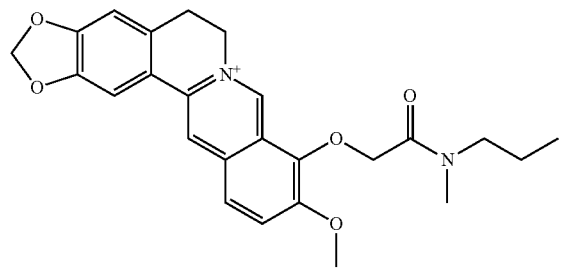

-continued

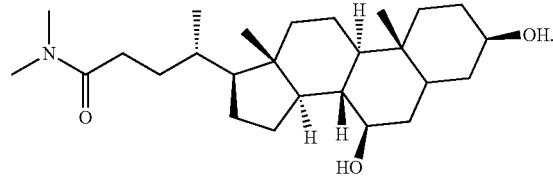

2. The method of claim 1, wherein said cancer treatable by NAB03 is a breast cancer.

3. The method of claim 1, wherein said cancer treatable by NAB03 is a liver cancer.

4. The method of claim 1, wherein said cancer treatable by NAB03 is a colorectal cancer.

5. The method of claim 1, wherein said cancer treatable by NAB03, when measured by CCK-8, has an IC50 of less than 10 uM when exposed to NAB03 for more than 48 hours.

6. The method of claim 1, wherein said cancer treatable by NAB03 is selected from the group consisting of the MDA468, PANC1, CCH, KMCH, Huh7, Huh2, and PC3 cell lines.

7. The method of claim 6, wherein said administering of said individual with said effective amount of NAB03 is an oral administration.

8. The method of claim 6, wherein said administering of said individual with said effective amount of NAB03 is an intravenous administration.

9. The method of claim 1, wherein said effective amount of NAB03 is between approximately 2 mg per kg of said individual and approximately 6 mg per kg of said individual.

10. The method of claim 9, wherein said effective amount of NAB03 is approximately 4 mg per kg of said individual.

* * * * *